United States Patent
Auerbach et al.

(10) Patent No.: US 10,183,096 B2
(45) Date of Patent: Jan. 22, 2019

(54) VALVE TREATMENT BY INJECTION

(71) Applicant: BIOSENSE WEBSTER (ISRAEL) LTD., Yokneam (IL)

(72) Inventors: Shmuel Auerbach, Kerem Maharal (IL); Ziyad Zeidan, Zemmer (IL); Michael David King, Kraainem (BE)

(73) Assignee: Biosense Webster (Israel) Ltd., Yokneam (IL)

( * ) Notice: Subject to any disclaimer, the term of this patent is extended or adjusted under 35 U.S.C. 154(b) by 242 days.

(21) Appl. No.: 14/978,240

(22) Filed: Dec. 22, 2015

(65) Prior Publication Data

US 2017/0172617 A1   Jun. 22, 2017

(51) Int. Cl.

| A61L 27/16 | (2006.01) |
|---|---|
| A61B 17/34 | (2006.01) |
| A61L 27/24 | (2006.01) |
| A61L 27/20 | (2006.01) |
| A61L 27/12 | (2006.01) |
| A61L 27/18 | (2006.01) |
| A61K 9/00 | (2006.01) |
| A61M 25/00 | (2006.01) |
| A61B 34/20 | (2016.01) |
| A61F 2/24 | (2006.01) |
| A61B 17/00 | (2006.01) |

(52) U.S. Cl.
CPC .......... *A61L 27/16* (2013.01); *A61B 17/3478* (2013.01); *A61K 9/0024* (2013.01); *A61L 27/12* (2013.01); *A61L 27/18* (2013.01); *A61L 27/20* (2013.01); *A61L 27/24* (2013.01); *A61B 2017/00243* (2013.01); *A61B 2017/3413* (2013.01); *A61B 2034/2063* (2016.02); *A61F 2/2442* (2013.01); *A61F 2002/249* (2013.01); *A61M 25/00* (2013.01); *A61M 2210/125* (2013.01)

(58) Field of Classification Search
CPC .......... A61L 27/12; A61L 27/16; A61L 27/18; A61L 27/20; A61L 27/24; A61B 17/3478; A61B 2034/2063; A61K 9/0024
See application file for complete search history.

(56) References Cited

U.S. PATENT DOCUMENTS

| 6,485,489 B2 | 11/2002 | Teirstein et al. |
|---|---|---|
| 7,229,469 B1 | 6/2007 | Witzel et al. |
| 8,328,798 B2 | 12/2012 | Witzel et al. |
| 9,011,531 B2 | 4/2015 | Rourke et al. |
| 2003/0069570 A1 | 4/2003 | Witzel et al. |

(Continued)

FOREIGN PATENT DOCUMENTS

| CA | 2660892 | 3/2007 |
|---|---|---|
| WO | WO 2004/032717 A2 | 4/2004 |

OTHER PUBLICATIONS

Silbiger, Jeffrey J., "Anatomy, mechanics, and pathophysiology of the mitral annulus," American Heart Journal, vol. 164, No. 2, pp. 163-176, Aug. 2012.

(Continued)

*Primary Examiner* — Thomas J Sweet
*Assistant Examiner* — Tiffany Shipmon

(57) ABSTRACT

A method for treating a valve of a heart of a subject is provided. The method includes inserting a needle into the heart, and, using the needle, injecting a soft-tissue-filling material into an annulus of the valve. Other embodiments are also described.

12 Claims, 3 Drawing Sheets

(56) References Cited

U.S. PATENT DOCUMENTS

| | | |
|---|---|---|
| 2005/0143811 A1 | 6/2005 | Realyvasquez |
| 2007/0232889 A1* | 10/2007 | Boese .................... A61B 6/463 600/407 |
| 2010/0087917 A1* | 4/2010 | Macha .................. A61F 2/2442 623/2.1 |
| 2012/0209376 A1 | 8/2012 | Hauser et al. |

OTHER PUBLICATIONS

Stuart, Mary, "Percutaneous Mitral Valve Therapy: The Next Decade", Start-Up, vol. 17, No. 2, Feb. 2012, pp. 1-18.

* cited by examiner

VALVE TREATMENT BY INJECTION

FIELD OF THE INVENTION

Embodiments of the present invention relate to the treatment of dilated annuluses that surround body orifices, such as dilated heart-valve annuluses.

BACKGROUND

US 2012/0209376, whose disclosure is incorporated herein by reference, describes methods for treating a defective mitral valve. One preferred method comprises attaching opposing ends of a tether to opposing regions of the mitral valve annulus. The tether is advanced percutaneously into the left atrium by a therapy catheter. Vacuum ports may be provided on the therapy catheter for grasping tissue along the mitral valve annulus. The therapy catheter may also include advanceable needles for passing the tether through the tissue. Alternatively, the ends of the tether may be attached to fastener elements which are secured to the tissue. Tension in the tether pulls the opposing regions of the mitral valve annulus into closer proximity for improving mitral valve function.

U.S. Pat. No. 6,485,489, whose disclosure is incorporated herein by reference, describes a catheter system and methods for repairing a valvular annulus or an annular organ structure of a patient comprising sandwiching and compressing the annulus and applying heat sufficient to shrink or tighten tissue surrounding the annulus defect.

US 2005/0143811, whose disclosure is incorporated herein by reference, describes methods and apparatus for valve repair. In one embodiment, the apparatus includes a first bridge portion and a second bridge portion. The apparatus may also include at least one base on each bridge portion. Attachment of the first bridge portion and the second bridge portion brings an anterior leaflet of the valve closer to the posterior leaflet and reduces a gap therebetween.

SUMMARY OF THE INVENTION

There is provided, in accordance with some embodiments of the present invention, a method for treating a valve of a heart of a subject. A needle is inserted into the heart, and, using the needle, a soft-tissue-filling material is injected into an annulus of the valve.

In some embodiments, the soft-tissue-filling material includes collagen.

In some embodiments, the soft-tissue-filling material includes hyaluronic acid.

In some embodiments, the soft-tissue-filling material includes calcium hydroxylapatite.

In some embodiments, the soft-tissue-filling material includes poly-L-lactic acid.

In some embodiments, the soft-tissue-filling material includes polymethylmethacrylate.

In some embodiments, the valve is a mitral valve.

In some embodiments, injecting the soft-tissue-filling material includes injecting the soft-tissue-filling material at two anterior sites located on an anterior portion of the annulus, and at a posterior site located on a posterior portion of the annulus.

In some embodiments, a first one of the two anterior sites is between a medial commissure of the annulus and cranialmost portion of the annulus, and a second one of the two anterior sites is between a lateral commissure of the annulus and the cranialmost portion of the annulus.

In some embodiments, the first one of the two anterior sites is caudally closer to the medial commissure than to the cranialmost portion of the annulus, and the second one of the two anterior sites is caudally closer to the lateral commissure than to the cranialmost portion of the annulus.

In some embodiments, the posterior site is opposite a cranialmost portion of the annulus.

In some embodiments, the valve is a tricuspid valve.

In some embodiments, the method further includes guiding the insertion of the needle, using ultrasound imaging.

In some embodiments, the method further includes guiding the injection of the soft-tissue-filling material, using ultrasound imaging.

In some embodiments, using the ultrasound imaging includes using intracardiac echocardiography.

In some embodiments,
guiding the injection of the soft-tissue-filling material includes, following a first injection of the soft-tissue-filling material, using Doppler ultrasound imaging, assessing an amount of retrograde flow through the valve, and
injecting the soft-tissue-filling material includes performing a second injection of the soft-tissue-filling material, in response to the assessment.

In some embodiments, the method further includes guiding the injection of the soft-tissue-filling material, using an electroanatomical mapping system.

In some embodiments, the needle is at a distal end of a catheter, and inserting the needle into the heart includes inserting the needle into the heart by inserting the catheter into the heart.

In some embodiments, inserting the needle into the heart includes inserting the needle into an atrium of the heart, and using the needle includes using the needle while the needle is in the atrium of the heart.

The present invention will be more fully understood from the following detailed description of embodiments thereof, taken together with the drawings, in which:

DETAILED DESCRIPTION OF EMBODIMENTS

Overview

In embodiments of the present invention, a heart valve is treated by injecting a soft-tissue-filling material into the annulus of the valve. For example, as described below, a catheter may be inserted into the heart, and a needle at a distal end of the catheter may be used to inject the material into the annulus. The soft-tissue-filling material causes the annulus to expand, thus bringing the leaflets of the valve closer together. Examples of suitable soft-tissue-filling materials include collagen, hyaluronic acid, calcium hydroxylapatite, poly-L-lactic acid, polymethylmethacrylate (e.g., polymethylmethacrylate beads or microspheres), any suitable combination of two or more of the above, and other suitable dermal fillers.

In some cases, the injected soft-tissue-filling material is absorbable, such that the effect of the injection is temporary. For example, in some cases, collagen fillers, the effects of which generally last for only a few months, are injected. Absorbable materials are appropriate for cases in which the pathology of the valve is only temporary, such as cases of temporary ischemia. In other cases, such as in cases of a more chronic pathology, a non-absorbable soft-tissue-filling material, such as polymethylmethacrylate, is injected.

The presently-described embodiments are advantageous, in that they do not require the implantation of a device in the subject. Moreover, the injection procedure is typically minimally invasive and relatively quick, and does not require that fluoroscopy be used, at least not for an extended period of time.

System and Method Description

Figure 1:
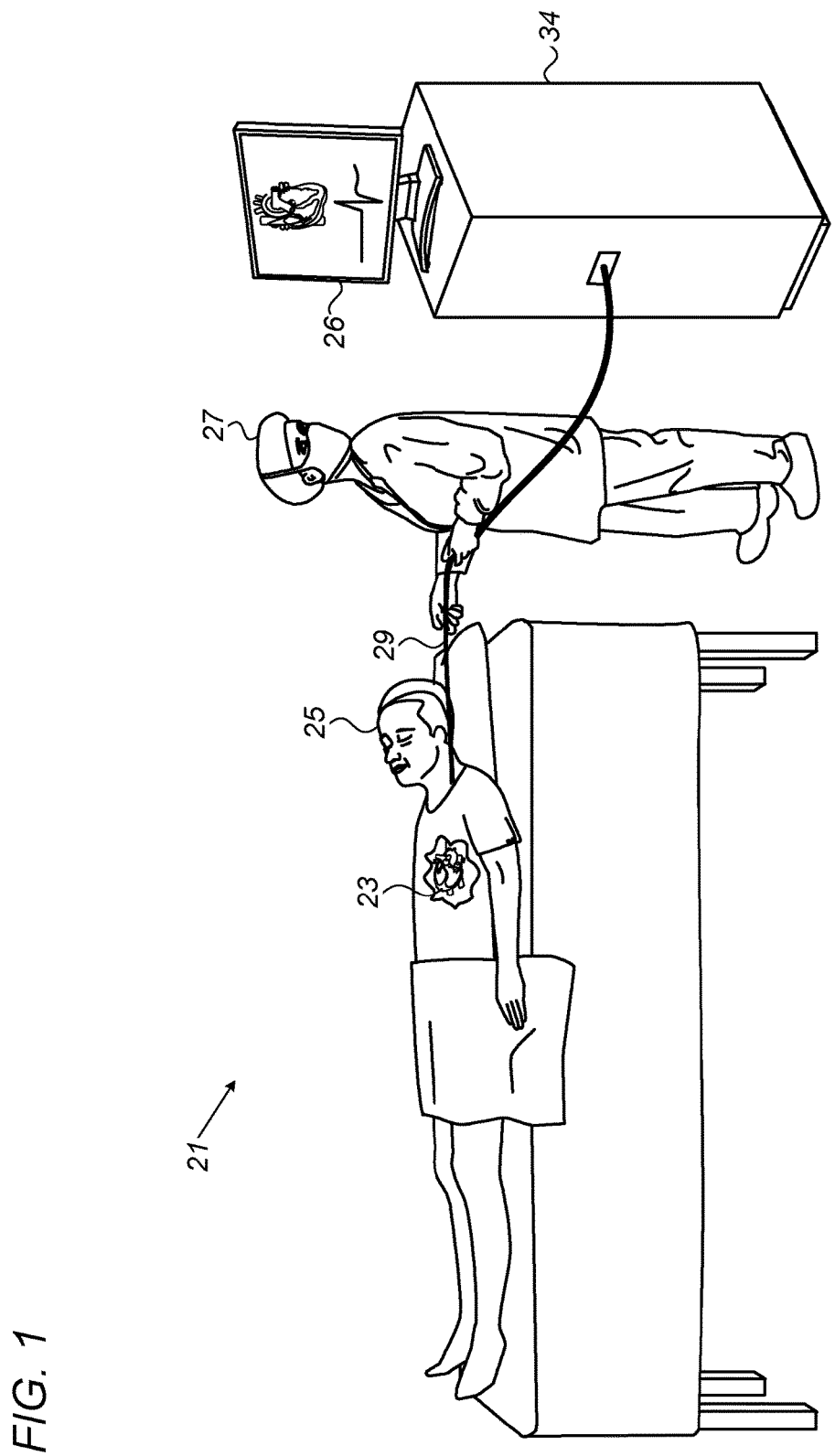
FIG. 1 is a schematic illustration of a system for treating a heart valve of a subject, in accordance with some embodiments of the present invention.

Reference is initially made to FIG. 1, which is a schematic illustration of a system 21 for treating a heart valve of a subject 25, in accordance with some embodiments of the present invention. System 21 comprises a catheter 29, which is connected to a console 34. A physician 27 inserts catheter 29 into the heart 23 of subject 25, and uses the catheter to treat the heart valve, as further described hereinbelow. During the procedure, for guidance, physician 27 may refer to a monitor 26, which shows relevant output, as further described hereinbelow.

Figure 2:
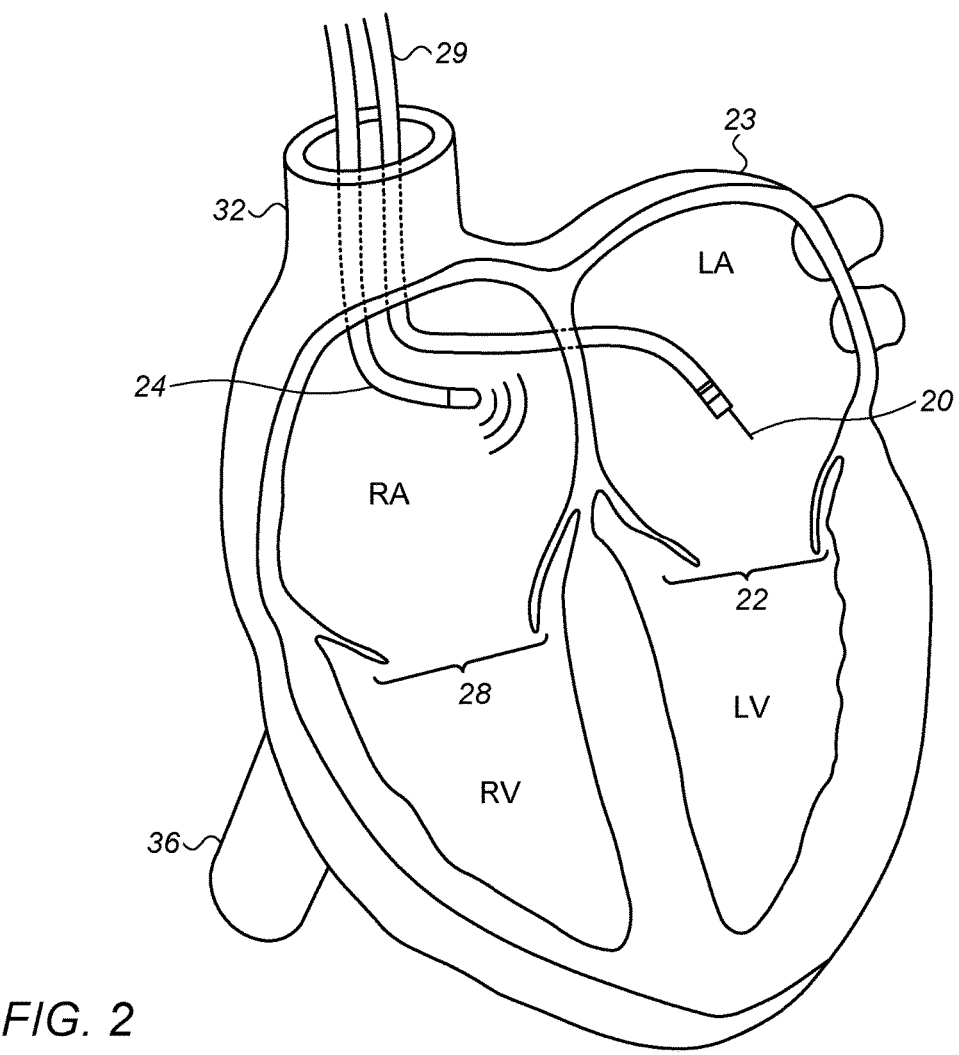
FIG. 2 shows the treatment of a mitral valve, in accordance with some embodiments of the present invention.

Reference is now made to FIG. 2, which shows the treatment of a mitral valve 22, which is situated between the left atrium (LA) and left ventricle (LV) of heart 23, in accordance with some embodiments of the present invention.

In embodiments of the present invention, a needle 20 at the distal end of catheter 29 is inserted into heart 23. For example, to treat mitral valve 22, the needle may be inserted into the left atrium of the heart. Subsequently, using needle 20, a soft-tissue-filling material is injected into the annulus of the valve at one or more sites. As further described below with reference to FIGS. 3A-B, the injection(s) at least partially correct the dilation of the annulus.

Although, in FIG. 2, needle 20 is shown entering heart 23 of the subject via the superior vena cava 32 of the subject, it is noted that the scope of the present disclosure includes inserting the needle in any other way, such as via the inferior vena cava 36. Furthermore, although the present figures depict the treatment of a mitral valve, it is noted that the scope of the present disclosure also includes treating a tricuspid valve 28, as well as other dilated annuluses surrounding other body orifices. For example, using methods described herein, a dilated sphincter muscle such as the gastroesophageal sphincter, duodenal gastric sphincter, anal sphincter, vesicoureteral sphincter, or urethral sphincter may be treated. The scope of the present disclosure also includes reducing the volume of a cavitary body organ, using methods described herein.

Typically, ultrasound imaging is used to guide the insertion of needle 20 and/or the injection of the soft-tissue-filling material. For example, intracardiac echocardiography may be used, by using an ultrasound transducer 24 that is inserted into the heart separately from catheter 29. (In such embodiments, ultrasound transducer 24 is typically situated in the right atrium (RA) or right ventricle (RV) of the heart during the procedure.) In some embodiments, an external ultrasound transducer is used, alternatively or additionally to using intracardiac echocardiography.

In yet other embodiments, alternatively or additionally to using ultrasound imaging, an electroanatomical mapping system, such as the CARTO® 3 System, available from Biosense Webster, Inc., 3333 Diamond Canyon Road, Diamond Bar, Calif. 91765, is used to guide the insertion of the needle and/or the injection of the soft-tissue-filling material. During the procedure, monitor 26 (FIG. 1) may show the physician relevant visual output from the ultrasound transducer and/or electroanatomical mapping system.

In some embodiments, following one or more of the injections, an assessment of valve function is performed, such as by using Doppler ultrasound (e.g., intracardiac Doppler ultrasound) to assess the amount of retrograde flow through the valve. If the amount of retrograde flow is sufficiently reduced, no more injections are performed. On the other hand, if the amount of retrograde flow has not been sufficiently reduced, one or more additional injections may be performed. (Typically, when multiple injections are performed, each of the injections is performed at a different respective site along the annulus.)

Figure 3A:
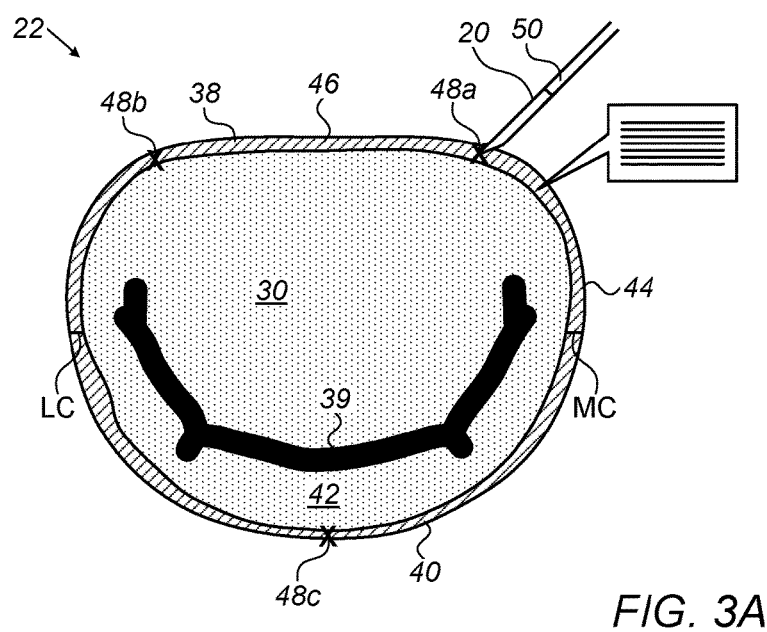
FIGS. 3A and 3B are schematic illustrations of, respectively, a mitral valve prior to and following treatment, in accordance with some embodiments of the present invention.
Figure 3B:
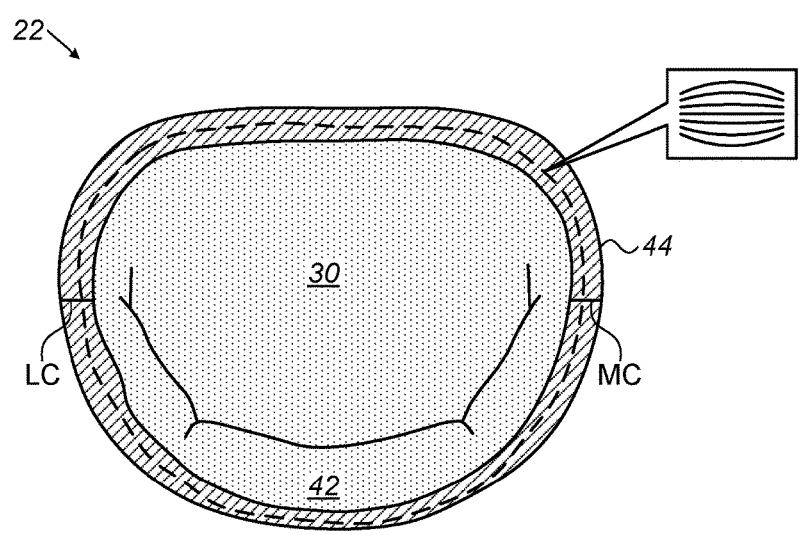

Reference is now made to FIG. 3A, which is a schematic illustration of a mitral valve 22 prior to treatment, and to FIG. 3B, which is a schematic illustration of the mitral valve following treatment, in accordance with some embodiments of the present invention.

Each of FIGS. 3A-B includes a caudally-facing view of the mitral valve, in which the annulus 44 of the valve is shown framing the anterior leaflet 30 and posterior leaflet 42 of the valve. Annulus 44 includes an anterior portion 38 (sometimes referred to as the "anterior annulus"), and a posterior portion 40 (sometimes referred to as the "posterior annulus"). Anterior portion 38 and posterior portion 40 are joined at the lateral commissure (LC) and medial commissure (MC). Annulus 44 is typically saddle-shaped, such that the anterior portion of the annulus, which includes the "riding horn" of the saddle, rises out of plane, in a cranial direction, from the rest of the annulus. (In FIGS. 3A-B, the cranial direction is out the page, toward the viewer.) The anterior portion of the annulus thus includes a cranialmost portion 46, typically situated at the center of the anterior portion.

As shown in FIG. 3A, prior to treatment, the mitral valve is dilated, such that there is a gap 39 between anterior leaflet 30 and posterior leaflet 42 upon the closing of the leaflets. Hence, during contraction of the left ventricle, blood flows from the left ventricle, in a retrograde manner, back into the left atrium.

FIG. 3B, on the other hand, shows the mitral valve following the injection of the soft-tissue-filling material. The soft-tissue-filling material causes the tissue of the annulus to expand, thus pushing the leaflets of the valve closer together and at least partially closing gap 39. The effect of the soft-tissue-filling material is depicted by the contrast between the inset portion of FIG. 3A, which includes a schematic representation of a portion of the tissue as it would appear under a microscope, and the inset portion of FIG. 3B, which shows the same portion of tissue following the filling of the portion by the injected material. To emphasize the expansion of the annulus, a dotted line in FIG. 3B marks the approximate location of the inner perimeter of annulus 44 prior to treatment.

Although FIG. 3B shows the expansion of the annulus as being approximately uniform, in some cases, the annulus expands more near the injection sites than at other sites. Hence, it is helpful to judiciously choose the injection sites, in order to reduce dilation of, and improve the mechanical function of, the annulus as much as possible. FIG. 3A shows one such judicious choice of three injection sites 48*a-c*, each site being marked with an "x" in the figure. Sites 48*a* and 48*b* are on the anterior portion 38 of the annulus; site 48*a* is between the medial commissure and cranialmost portion 46, while site 48*b* is between the lateral commissure and cranialmost portion 46. Site 48*c* is on the posterior portion 40 of the annulus, opposite cranialmost portion 46.

In one embodiment, sites 48*a* and 48*b* lie toward the bottom of the riding horn, such that they are situated roughly in-plane with the majority of the annulus. In other words, site 48*a* is caudally closer to the medial commissure than to the cranialmost portion of the annulus, and site 48*b* is caudally closer to the lateral commissure than to the cranialmost portion of the annulus.

In some embodiments, the above-described assessment of valve function is performed only after the soft-tissue-filling material is injected at all three sites. If the amount of retrograde flow has not been sufficiently reduced, one or more additional injections are performed at additional sites. In other embodiments, the assessment is performed after one or two injections at one or two of the three sites, and, if the valve is functioning properly, the remaining injection(s) might not be performed. (For the sake of illustration, in FIG. 3A, the beginning of the first injection is depicted, in that a soft-tissue-filling material 50 is shown flowing down through needle 20, which penetrates the annulus at site 48*a*.)

Notwithstanding the above, it is noted that the scope of the present disclosure includes the injection of any suitable soft-tissue-filling material(s) at any suitable site(s) along the annulus, alternatively or additionally to the sites shown in FIG. 3A.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. A method for treating a mitral valve of a heart of a subject, the method comprising:
   inserting a needle into the heart;
   using the needle, injecting a soft-tissue-filling material at only two anterior sites located on an anterior portion of an annulus of the mitral valve, and at only one posterior site located on a posterior portion of the annulus,
   wherein a first one of the two anterior sites is between a medial commissure of the annulus and a cranial most portion of the annulus, and wherein a second one of the two anterior sites is between a lateral commissure of the annulus and the cranial most portion of the annulus and the first one of the two anterior sites is caudally closer to the medial commissure than to the cranial most portion of the annulus, and the second one of the two anterior sites is caudally closer to the lateral commissure than to the cranial most portion of the annulus; and
   guiding the injection of the soft-tissue-filling material for the injecting step, using an electroanatomical mapping system.

2. The method according to claim 1, wherein the soft-tissue-filling material includes collagen.

3. The method according to claim 1, wherein the soft-tissue-filling material includes hyaluronic acid.

4. The method according to claim 1, wherein the soft-tissue-filling material includes calcium hydroxyapatite.

5. The method according to claim 1, wherein the soft-tissue-filling material includes poly-L-lactic acid.

6. The method according to claim 1, wherein the soft-tissue-filling material includes polymethylmethacrylate.

7. The method according to claim 1, further comprising guiding the insertion of the needle, using ultrasound imaging.

8. The method according to claim 1, further comprising guiding the injection of the soft-tissue-filling material, using ultrasound imaging.

9. The method according to claim 8, wherein using the ultrasound imaging comprises using intracardiac echocardiography.

10. The method according to claim 8,
    wherein guiding the injection of the soft-tissue-filling material comprises, following a first injection of the soft-tissue-filling material, using Doppler ultrasound imaging, assessing an amount of retrograde flow through the valve, and
    wherein injecting the soft-tissue-filling material comprises performing a second injection of the soft-tissue-filling material, in response to the assessment.

11. The method according to claim 1, wherein the needle is at a distal end of a catheter, and wherein inserting the needle into the heart comprises inserting the needle into the heart by inserting the catheter into the heart.

12. The method according to claim 1, wherein inserting the needle into the heart comprises inserting the needle into an atrium of the heart, and wherein using the needle comprises using the needle while the needle is in the atrium of the heart.

* * * * *